United States Patent
Simon et al.

(10) Patent No.: US 8,021,645 B2
(45) Date of Patent: *Sep. 20, 2011

(54) SYNTHESIS OF HUMAN SECRETORY IGA AND IGM AND THE FORMATION OF A MEDICAMENT THEREFROM

(76) Inventors: Michael R. Simon, Ann Arbor, MI (US); Stephanie M. Chervin, Ann Arbor, MI (US); Stephen C. Brown, Ann Arbor, MI (US)

( * ) Notice: Subject to any disclaimer, the term of this patent is extended or adjusted under 35 U.S.C. 154(b) by 380 days.

This patent is subject to a terminal disclaimer.

(21) Appl. No.: 12/138,758

(22) Filed: Jun. 13, 2008

(65) Prior Publication Data

US 2008/0260822 A1   Oct. 23, 2008

Related U.S. Application Data

(63) Continuation-in-part of application No. 11/851,606, filed on Sep. 7, 2007, now Pat. No. 7,794,721, which is a continuation-in-part of application No. 11/839,781, filed on Aug. 16, 2007, now Pat. No. 7,597,891, which is a continuation-in-part of application No. 11/610,154, filed on Dec. 13, 2006, now abandoned.

(51) Int. Cl.
*A61K 49/00* (2006.01)
*A61K 39/02* (2006.01)
*A61K 39/08* (2006.01)

(52) U.S. Cl. .... 424/9.2; 424/9.1; 424/130.1; 424/139.1; 424/140.1; 424/150.1; 424/178.1; 424/234.1; 424/236.1; 424/239.1

(58) Field of Classification Search ................... 424/9.1, 424/9.2, 130.1, 139.1, 140.1, 150.1, 178.1, 424/234.1, 236.1, 239.1
See application file for complete search history.

(56) References Cited

U.S. PATENT DOCUMENTS 5,773,000 A * 6/1998 Bostwick et al. .......... 424/167.1

OTHER PUBLICATIONS

Kelly C.P., Eur. Jour. Gastroenterol. Hepaol., vol. 8, No. 11, pp. 1048-1053, 1996.*
Alfred E. Bacon III et al., Immunoglobulin G Directed Against Toxins A and B of Clostridium Difficile in The General Population and Patients With Antibiotic-Associated Diarrhea; 1994; pp. 205-209; DIAGN Microbiol Infect Dis.
L.A. Barroso et al.; Nucleotide Sequence of Clostridium Difficile Toxin B Gene; Nucleic Acids Research, vol. 18, No. 13; 1990; Oxford University Press.
Jay A. Berzofsky, et al., Antigen-Antibody Interactions and Monoclonal Antibodies; Fundamental Immunology, Third Edition; 1993; pp. 421, 455-464; Raven Press Ltd., New York.

Mary Boesman-Finkelstein, et al., Bovine Lactogenic Immunity Against Cholera Toxin-Related Enterotoxins and Vibrio Cholerae Outer Membranes; Infection and Immunity; 1989; pp. 1227-1234; American Society for Microbiology.
Harald Brussow et al., Bovine Milk Immunoglobulins for Passive Immunity to Infantile Rotavirus Gastroenteritis; Journal of Clinical Microbiology, Jun. 1987; pp. 982-986; American Society for Microbiology.
Lawrence A. Cone, MD et al., A Durable Response To Relapsing Clostridium Difficile Colitis May Require Combined Therapy with High-dose Oral Vancomycin and Intravenous Immune Globulin; Infectious Diseases in Clinical Practice; vol. 4, No. 4, 2007; pp. 217-220.
B. Corthesy; Recombinant Secretory IGA For Immune Intervention Against Mucosal Pathogens; Immunoglobulins and Mechanisms of Mucosal Immunity; Biochem Soc Trans; 1997; 471-475.
G. Corthier et al.; Emergence in Gnotobiotic Mice of Nontoxinogenic Clones of Clostridium Difficile from a Toxinogenic One; Infection and Immunity, Jun. 1988; pp. 1500-1504; vol. 56, No. 6.
G. Corthier et al.; Protection Against Experimental Pseudomembranous Colitis in Gnotobiotic Mice by Use of Monoclonal Antibodies Against Clostridium Difficile Toxin A; Infection and Immunity, Mar. 1991; pp. 1192-1195; vol. 59, No. 3.
Pascal Crottet et al; Expression, Purification and Biochemical Characterization of Recombinant Murine Secretory Component: A Novel Tool in Mucosal Immunology; Biochem Society J: 1999; pp. 299-306.
C.H. Dove et al., Molecular Characterization of the Clostridium Difficile Toxin A Gene; Infection and Immunity; Feb. 1990; pp. 480-488; vol. 58, No. 2.
Marion Ehrich et al., Production of Clostridium Difficile Antitoxin; Infection and Immunity; Jun. 1980; pp. 1041-1043; vol. 28, No. 3.
Ronald Fayer et al.; Immunotherapeutic Efficacy of Bovine Colostral Immunoglobulins from a Hyperimmunized Cow against Cryptosporidiosis in Neonatal Mice; Infection and Immunity, Sep. 1990; pp. 2962-2965; vol. 58, No. 9.
Dale N. Gerding; Clostridium Difficile-Associated Diarrhea and Colitis in Adults; A Prospective Case-Controlled Epidemilogic Study; Arch Intern Med; vol. 146, Jan. 1986.

(Continued)

*Primary Examiner* — Rodney P. Swartz
(74) *Attorney, Agent, or Firm* — Patent Procurement Services

(57) ABSTRACT

A composition for treating a subject is provided. The composition includes antigen specific dimeric secretory IgA and pentameric IgM therapeutic. A process for manufacturing a medicament for the treatment of *C. difficile* associated disease in a human is also provided that the modification of antigen specific dimeric secretory IgA and pentameric IgM with secretory component to form a antigen specific dimeric secretory IgA and pentameric secretory IgM therapeutic. The antigen specific dimeric secretory IgA and the pentameric secretory IgM therapeutic is then mixed with formulating agents to create a capsule, tablet, liquid or suppository dosing form. The therapeutic is amenable to enrobement directly through microencapsulation or the dosing form is coated with an enteric coating. A method of *C. difficile* treatment with the therapeutic is also provided that is amenable to supplementation with concurrent or prior antibiotic administration.

17 Claims, No Drawings

OTHER PUBLICATIONS

Helmut Hilpert et al.; Use of Bovine Mild Concentrate Containing Antibody to Rotavirus to Treat Rotavirus Gastroenteritis in Infants; The Journal of Infectious Diseases; vol. 156, No. 1: Jul. 1987; pp. 158-166.

Robert M.L. Jones et al.; Thiol-Disulfide Redox Buffers Maintain a Structure of Immunoglobulin A that is Essential For Optimal in Vitro Binding to Secretory Component; Biochimica et Biophysica; 1998; pp. 265-274.

Ciaran P. Kelly et al; Clostridium Difficile Collitis. NEJM—Clostridium Difficile Collitis; pp. 1-17.

Ciaran P. Kelly et al.; Human Colonic Aspirates Containing Immunoglobulin A Antibody to Clostridium Difficile Toxin A Inhibit Toxin A—Receptor Binding; 1992; The American Gastroenterological Association; pp. 35-40.

Donald Y.M. Leung et al; Treatment with Intravenously Administered Gamma Globulin of Chronic Relapsing Colitis Induced by Clostridium Difficile Toxin; From the Division of Pediatric Allergy-Immunology; pp. 633-637.

Jeffrey M. Libby et al.; Effects of the Two Toxins of Clostridium Difficile in Antibiotic-Associated Cecitis in Hamsters; Infection and Immunity; May 1982; pp. 822-829.

Aldo A.M. Lima et al., Effects of Clostridium Difficile Toxins A and B in Rabbit Small and Large Intestines in Vivo and on Cultured Cells In Vitro; Infection and Immunity; Mar. 1988; pp. 582-588; vol. 56, No. 3.

Thomas J. Louie et al.; Tolevamer.; a Novel Nonantibiotic Polymer, Compared with Vancomycin in the Treatment of Mild to Moderately Sever Clostridium Difficile-Associated Diarrhea; Clinical Infectious Diseases; 2006; pp. 411-420.

Elke Lullau et al; Antigen Binding Properties of Purified Immunoglobulin A and Reconstituted Secretory Immunoglobulin A Antibodies; The Journal of Biological Chemistry; pp. 16300-16309.

David M. Lyerly et al.; Clostridium Difficile; Its Disease and Toxins; Clinical Microbiology Review, Jan. 1988; pp. 1-18.

David M. Lyerly et al.; Characterization of Toxins A and B Clostridium Difficile with Monoclonal Antibodies; Infection and Immunity, Oct. 1986; pp. 70-76; vol. 54, No. 1.

David M. Lyerly et al.; Passive Immunzation of Hamsters against Disease Caused by Clostridium Difficile by Use of Bovine Immunoglobulin G Concentrated; Infection and Immunity, Jun. 1991; pp. 2215-2218; vol. 59, No. 6.

D.M. Lyerly et al.; Biological Activities of Toxins A and B of Clostridium Difficile; Infection and Immunity Mar. 1982; pp. 1147-1150.

David M. Lyerly et al.; Effects of Clostridium Difficile Toxins Given Intragastrically to Animals; Infection And Immunity Feb. 1985; pp. 349-352; vol. 47; No. 2.

S. Mahe et al; Effect of Various Diets on Toxin Production by Two Strains of Clostridium Difficile in Gnotobiotic Mice; Infecion And Immunity, Aug. 1987; pp. 1801-1805; vol. 55, No. 8.

Ramon D. Martinez et al.; Purification and Characterization of Clostridium Sordellii Hermorrhagic Toxin and Cross-Reactivity with Clostridium Difficile Toxin A (Enterotoxin) Infection and Immunity; May 1988; pp. 1215-1221: vol. 56, No. 5.

Lynne V. McFarland et al.; Nosocomial Acquistion of Clostridium Difficile infection; The New England Journal of Medicine; pp. 204-210.

Lynne V. McFarland et al; Review of Clostridium Difficile-Associated Disease; American Journal of Infection Control; vol. 14, No. 3; Jun. 1986; pp. 99-109.

Stuart McPherson et al; Intravenous Immunoglobulin for the Treatment of Severe, Refractory, and Recurrent Clostridium Diarrhea; Disease of the Colon & Rectum; The American Socity of Colon and Rectal Surgeons; pp. 640-645.

C. Mietens et al; Treatment of Infantile *E. coli* Gastroenteritis With Specific Bovine Anti-E, Coli Milk Immunoglobulins; European Journal of Pediatrics: 1979; pp. 239-252.

T. J. Mitchell et al; Effect of Toxin A and B of Clostridium Difficile on Rabbit Ileum and Colon; Gut, 1986; pp. 78-85.

Charalabos Pothoulakis et al; Characterization of Rabbit Ileal Receptors for Clostridium Difficile Toxin A; Evidence For A Receptor—Coupled G Protein; Ileal Receptor for Toxin A, pp. 119-125.

Sara E. Rothman et al; Differential Cytotoxic Effects of Toxins A and B Isolated From Clostridium Difficile; Infection and Immunity; Nov. 1984; pp. 324-331.

Jindrich Symersky et al; Expression of the Recombinant Human Immunoglobulin J Chain In *Escherichia coli* 2000; Molecular Immunology; pp. 133-140.

Carol O. Tacket et al; Protection By Milk Immunoglobulin Concentrate Against Oral Challenge With Enterotoxigenic *Escherichia coli*; the New England Journal of Medicine; May 1988; pp. 1240-1243.

J. Salcedo et al; Intravenous Immunoglobulin Therapy For Severe Clostridium Difficlle Colitis; gut.bmj.com; Dec. 2006; pp. 366-370.

Kenneth D. Tucker et al; Toxin A of Clostridium Difficile Is A Potent Cytoxin; Journal of Clinical Microbiology; pp. 869-871; vol. 28, No. 5.

R. Weltzin et al; Intranasal Monoclonal IGA Antibody to Respiratory Synctial Virus Protects Rhesus Monkeys Against Upper And Lower Respiratory Tract Infection; pp. 256-261.

Richard Weltzin et al; Intranasal Monoclonal Immunoglobuln A Against Respiratory Syncytial Virus Protects Against Upper and Lower Respiratory Tract Infections in Mice; Antimicrobial Agents and Chemotherapy; Dec. 1994; pp. 2785-2791.

Y. Yoshiyama et al; Specific Antibodies to Cholera Toxin In Rabbit Milk Are Protective Against Vibrio Cholerae-Induced Intestinal Secretion; Immunology; 1987: pp. 543-547.

L.A. Barroso et al; Nucleotide Sequence of Clostridium Difficile Toxin B Gene; Nucleic Acids Research, vol. 18, No. 13: pp. 4004.

Stuart Johnson et al; Selective Neutralization of a Bacterial Enterotoxin by Serum Immunoglobulin A in Response to Mucosal Disease; Infection and Immunity; Aug. 1995; pp. 3166-3173; vol. 63; No. 8.

Jon B. Morris et al; Role of Surgery in Antibiotic-Induced Pseudomembranous Enterocolitis; The American Journal of Surgery; vol. 160; Nov. 1990; pp. 535-539.

Hiltrud Strubbe et al; Polymeric IGA Is Superior to Monomeric IGA and IGG Carrying The Same Variable Domain in Preventing Clostridium Difficile Toxin A Damaging of T84 Monolayers; The American Association of Immunologists: 2000; pp. 1952-1960.

Marina S. Morgan et al; The Lancet; vol. 341; Mar. 1993; pp. 701, 702, 1036.

George Triadafilopoulos et al; Differential Effects of Clostridium Difficile Toxins A and B on Rabbit Ileum; 1987; vol. 93; The American Gastroenterolocial Association; pp. 273-279.

Mark H. Wilcox; Descriptive Study of Intravenous Immunoglobulin for The Treatment of Recurrent Clostridium Difficile Diarrhoea; Journal of Antimicrobial Chemotherapy; 2004; pp. 882-884.

J.L. Oncley et al; The Separation of the Antibodies, Isoagglutinins, Prothrombin, Plasminogen and B1-Lipoprotein Into Subfractions of Human Plasma; Journal of The American Chemical Society; Feb. 1949; vol. 71; No. 2.

* cited by examiner

SYNTHESIS OF HUMAN SECRETORY IGA AND IGM AND THE FORMATION OF A MEDICAMENT THEREFROM

CROSS REFERENCE TO RELATED APPLICATIONS

This application is a continuation-in-part of U. S. patent application Ser. No. 11/851,606 filed Sep. 7, 2007 now U.S. Pat. No. 7,794,721 which in turn is a continuation-in-part of U.S. patent application Ser. No. 11/839,781 filed Aug. 16, 2007; now U.S. Pat. No. 7,597,891; which in turn is a continuation-in-part of U.S. patent application Ser. No. 11/610,154 filed Dec. 13, 2006; abandoned; the contents of these applications are hereby incorporated by reference.

FIELD OF THE INVENTION

This invention relates in general to compositions for the treatment of *Clostridium difficile* associated diseases such as *Clostridium difficile* colitis, pseudomembranous colitis and antibiotic associated diarrhea and in particular to secretory immunoglobulin A and immunoglobulin M (IgA and IgM) compositions administered in the form of pharmaceutical compositions.

BACKGROUND OF THE INVENTION

*Clostridium difficile* (*C. difficile*) is a gram-positive anaerobic bacillus and is the causal agent of antibiotic-associated pseudomembranous colitis in humans and other mammals. Antibiotic associated pseudomembranous colitis results from the use of broad-spectrum antibiotic agents such as clindamycin that have been administered to treat a primary bacterial infection. The antibiotic therapy often leads to the destruction of endogenous intestinal flora which allows for the colonization of *C. difficile* in the gut leading to the observed diarrhea in about 10% of treated patients and pseudomembranous colitis in about 1% of treated patients. *C. difficile* causes antibiotic associated diarrhea and almost all cases of pseudomembranous colitis.

The colitis of *Clostridium difficile*-associated disease results from the synergistic action of *C. difficile* toxin A and toxin B upon the colon mucosa (Barroso et al., 1990; Dove et al., 1990; Lyerly et al., 1988). Together, the toxins disrupt cell-cell tight junctions of the colon thereby allowing the bacterium to adhere to the underlying colon tissue and feed upon the nutrients released by the damaged epithelium (Borriello, 1998). Successive rounds of *C. difficile* colonization, replication, and toxin production lead to a vigorous host inflammatory response resulting in further degradation of the gut tissue, the pseudomembranous pathology associated with the diarrhea and the pain observed in *Clostridium difficile*-associated disease.

Most patients with *C. difficile* associated disease are treated effectively with vancomycin or metronidazole. Non-antibiotic treatment modalities that have been investigated include tolevamer, a toxin binding polymer (Louie et al., 2006), and an antiparasitic medication, nitazoxanide (Bartlett, 2006). However, relapses occur in about 20-25% of patients. Therefore, there is still a need for additional effective treatments of *Clostridium difficile* associated disease in humans.

Immunological treatment is valuable because vaccination against toxins A and B stimulates active immunity against *C. difficile* disease in animals (Libby et al., 1982). However, vaccines against the organism and its toxins are not available for human use.

Passive immunization is another immunological treatment. Studies indicate that such passive immunization provides protection (Boesman-Finkelstein et al., 1989; Brussow et al., 1987; Fayer et al., 1990; Hilpert et al., 1987; Mietens et al., 1979; Tacket et al., 1988; Yoshiyama and Brown, 1987). Serum antibodies against *C. difficile* protect hamsters against *C. difficile* disease after oral administration. Passive immunization with bovine antibodies has been proposed as a treatment for other infectious diseases of the gastrointestinal tract, such as diseases caused by rotavirus, enteropathogenic and enterotoxigenic *Escherichia coli, Vibrio cholerae*, and *Cryptosporidium parvum*. It has been reported that bovine immunoglobulin G (IgG) concentrate from the colostrum of cows vaccinated with *C. difficile* toxoid protects hamsters against antibiotic associated cecitis. The hamsters were protected when treated before the onset of diarrhea but not after diarrhea began (Lyerly et al., 1991). IgG directed against toxins A and B of *C. difficile* are present in the general population (Bacon and Fekety, 1994). Human intravenous immunoglobulin derived from plasma donors has facilitated treatment in some patients, especially patients who lack circulating antibodies to the *C. difficile* toxins (Cone et al., 2006; Leung et al., 1991; McPherson et al., 2006; Salcedo et al., 1997; Wilcox, 2004).

In vitro experiments have demonstrated that polymeric immunoglobulins are superior to monomeric immunoglobulin in preventing *C. difficile* toxin damage to intestinal epithelial cell monolayers (Stubbe et al., 2000). Selective neutralization of *C. difficile* toxin by serum IgA has also been demonstrated (Johnson et al., 1995). Administration of an immunoglobulin product containing specific antibodies to *C. difficile* results in the elimination of *C. difficile* toxins and also killing of the bacteria within the colon as detailed in U.S. Pat. No. 5,773,000. Such passive immunization therefore provides an effective approach for the treatment of *C. difficile* associated diseases such as colitis, pseudomembranous colitis and antibiotic associated diarrhea. This is especially important for patients experiencing multiple relapses.

Current treatments for *C. difficile* associated disease use antibiotics such as metronidazole and vancomycin. These drugs result in further disruption of the intestinal flora and are associated with a 20-25% incidence of disease relapse.

As reported by Tjellstrom, monomeric polyclonal IgA admixed with polyclonal IgG (2:1) derived from plasma (Ig-Abulin, Immuno, Vienna) (100 mg/mL) when administered orally 3 times daily in 4 mL doses for 3 weeks to a three and one-half year old child with antibiotic-associated diarrhea and *C. difficile* toxin A in his stools with concurrent vancomycin administration caused improvement (Tjellstrom et al., 1993). Polyclonal IgG derived from pooled plasma was administered to a second child with refractory *C. difficile* diarrhea who had failed treatment with antibiotics and intravenous polyclonal IgG. This patient received oral polyclonal IgG at 200mg/kg/day every 2 days for 3 doses together with courses of oral vancomycin and Lactobacillus. The child had recovered at follow-up evaluation 2 weeks later (Saturna at al. 2006). These reports demonstrate the efficacy of oral passive immunization with pooled immunoglobulins derived from the general population. It appears that monomeric circulatory immunoglobulins possess efficacy. However, increased efficacy is achieved by dimeric secretory IgA and pentameric secretory IgM owing to the propensity of monomeric circulatory immunoglobulins to degrade in the gastrointestinal tract. The dosing requirements of monomeric immunoglobulins therefore increase treatment costs. The prior art use of circulatory immunoglobulins failed to explore antigen specific secretory IgA and IgM as a potential medicament.

It is recognized that the large majority of the total IgA fraction is not specific for toxins A or B. As a result, this major fraction may be of little clinical value for the treatment of *C. difficile* associated disease. Therefore, further chemical refinement of this bulk material may be uneconomical in terms of reagent costs and effort. In addition, higher toxin binding titers are achieved with isolated *C. difficile* antitoxin-specific IgA, as compared to bulk IgA.

Thus, there exists a need for an antigen specific IgA and IgM therapeutic that is resistant to gastrointestinal tract degradation. There also exists a need to provide such a therapeutic in a dosing form well suited for treating an infected subject.

SUMMARY OF THE INVENTION

A composition for treating a subject, especially a human subject, is provided. The composition includes an antigen specific dimeric IgA or a pentameric IgM therapeutic that is formed by combining antigen specific polyclonal dimeric IgA or pentameric IgM containing J chain with a recombinant secretory component in a molar ratio of the antigen specific dimeric IgA or antigen specific pentameric IgM to the secretory component of 1:1. Formulating agents are mixed with the dimeric IgA or pentameric IgM to yield a dosing form of a capsule, tablet, liquid or a suppository. The IgA or IgM therapeutic is optionally enterically coated or microencapsulated to withstand gastrointestinal exposure associated with oral delivery. The dosing form is in a daily amount of between 0.1 and 50 grams. The dosing form containing the IgA or IgM therapeutic optionally also includes an antibiotic.

A process for manufacturing a medicament for the treatment of *C. difficile* associated disease in a human is also provided that includes the collection or purification of antigen specific polyclonal dimeric IgA or pentameric IgM as a byproduct of cold ethanol fractionation of pooled plasma derived from more than one human individual. The polyclonal antigen specific polyclonal dimeric IgA or pentameric IgM is subjected to antiviral treatment to yield a virus free polyclonal antigen specific polyclonal dimeric IgA or pentameric IgM that is also sterilized. The antigen specific polyclonal dimeric IgA or pentameric IgM regardless of origin is modified with secretory component to form a secretory antigen specific polyclonal dimeric IgA or pentameric IgM therapeutic. The antigen specific polyclonal dimeric IgA or pentameric secretory IgM therapeutic is then mixed with formulating agents to create a capsule, tablet, reconstituted solution, or suppository dosing form. The pooled plasma is optionally derived from specifically immune or immunized donors. The therapeutic is amenable to enrobement directly through microencapsulation or the dosing form is coated with an enteric coating. A method of treatment for *C. difficile* with the therapeutic is also provided. The treatment is amenable to supplementation with concurrent or prior antibiotic administration.

DETAILED DESCRIPTION OF THE PREFERRED EMBODIMENTS

The present invention has utility as a treatment for *C. difficile* infections. Unlike prior usage of monomeric IgA and IgG that is susceptible to gastrointestinal degradation, the present invention uses antigen specific polyclonal dimeric secretory IgA or pentameric secretory IgM. Because of its resistance to degradation in the gastrointestinal tract, it can be used at lower doses. Antigen specific polyclonal dimeric IgA or pentameric IgM according to the present invention are bound to secretory component in order to mimic secretory IgA and IgM endogenous to the subject.

The present invention is superior to polymeric immunoglobulins administered orally because of the presence of secretory component protects the antigen specific IgA and IgM from digestion in the gastrointestinal tract. Polyclonal immunoglobulins, including antigen specific polyclonal dimeric IgA and polyclonal pentameric IgM, directed against toxins A and B of *C. difficile* are present in the general population and are currently discarded as an unwanted byproduct of the manufacture of intravenous immunoglobulin. The present invention affords a prophylactic or active treatment of *C. difficile* disease alone, or in conjunction with a synergistic antibiotic. Current treatment of *C. difficile* associated disease is plagued by an unacceptable failure rate and antibiotic retreatment of patients with *C. difficile* associated disease results in the acquisition of additional unwanted antibiotic resistance.

As used herein, a "subject" is defined as a mammal and illustratively includes humans, non-human primates, horses, goats, cows, sheep, pigs, dogs, cats, and rodents.

As the present invention uses an immunoglobulin rather than antibiotics, an effective treatment is provided which does not disturb the intestinal flora.

The following description of the preferred embodiment(s) is merely exemplary in nature and is in no way intended to limit the invention, its application, or uses.

In one embodiment, the invention provides a method for medical treatment of humans involving the oral administration of a secretory IgA and IgM component that can be derived from a number of sources. One such source for the IgA and IgM is pooled human plasma following Coin cold ethanol fractionation to produce fraction III precipitate as performed by those of skill in the art of protein separation. IgA and IgM byproduct is further purified by adsorption onto an ion exchange medium in neutral or slightly acidic conditions as performed by those of skill in the art of protein purification.

A more detailed description of isolation of an IgA and IgM component as a byproduct from pooled human plasma or hyperimmune pooled human plasma is as follows. Ethanol fractionation of pooled human plasma is a well-known process to prepare immunoglobulin G. Pooled human plasma is first obtained from licensed plasmapheresis centers in the United States and tested for various pathogens including the HIV virus. The first manufacturing step of most commercial immunoglobulin G preparations involves a modified cold ethanol fractionation according to Cohn to produce Cohn fraction II. In the fractionation process, many infectious viruses are eliminated from the pooled human plasma. Following fractionation, the Cohn fraction II is subjected to adsorption onto an ion exchange medium. This step significantly reduces the IgA and IgM concentrations. Such a step is important for producing immunoglobulin G for intravenous infusion into humans. This is because some individuals undergo anaphylactic-like reactions if treated with intravenous IgG that contains IgA or IgM as an impurity.

The modified cold ethanol fractionation process according to Cohn is a series of fractionations using various levels of ethanol, pH, and temperature to produce a fraction II which is further treated to produce immunoglobulins as described above. In the fractionation method, pooled human plasma is first treated to produce a cryoprecipitate and cryo-supernatant. The cryo-supernatant is subjected to a first ethanol fractionation to yield a supernatant I. Supernatant I is subjected to a second ethanol fractionation to yield fraction II+III. Fraction II+III is subjected to a third ethanol fractionation procedure to yield a supernatant III and Fraction III precipitate.

The fraction III precipitate enriched in IgA and IgM is generally discarded as an unwanted byproduct. According to the invention, this unwanted IgA and IgM following ion exchange adsorption purification is further treated by incubation with immobilized hydrolases to inactivate viruses and vasoactive substances. Such treatment has been proven to eliminate many viruses tested including HIV, Sindbis, and vaccinia. Other antiviral treatments, as known to those skilled in the art, are used in combination and consist of solvent detergent processes, nanofiltration and/or heat inactivation. Usually three antiviral steps are implemented. Following incubation to remove viruses, the concentration of the active material is adjusted with sterile saline or buffered solutions to ensure a constant amount of active material per milliliter of reconstituted product. Finally, the solution with a constant amount of reconstituted product is sterilized by filtration before use.

The ethanol fractionation process according to Cohn is well known in the art (Cohn et al., 1946; Oncley et al., 1949; Strong, 1963), and in most detail [see pages 576-602, Kirk-Othmer Encyclopedia of Chemical Technology, Vol. 3, second edition (1963)]. Alternatively, ion exchange chromatography may be used to obtain the dimeric IgA and pentameric IgM byproduct during the manufacture of intravenous immunoglobulin. From 5% to 22% of plasma IgA is dimeric (Stubbe et al., 2000) and from 5% to 10% of plasma IgM is pentameric IgM (Delacroix et al. 1981; Delacroix et al. 1983; Carayannopoulos and Capra 1993), The resulting dimeric IgA-J chains and the pentameric IgM-J chains are purified.

Preparations of IgA and IgM derived from human plasma or serum are enriched in *C. difficile* toxin A and toxin B specific antibodies by affinity purification methods. Affinity purification methods have a long established history isolating various specific ligand-binding macromolecules from complex biofluid and tissue extracts. In this case, *C. difficile* toxins A and B are immobilized to an appropriate solid-phase support such as Sepharose 4B, with which re-suspended Cohn fraction III precipitate or jacalin-purified IgA solutions will be incubated, then washed extensively. Proteins binding only *C.defficile* toxins A and B will be eluted using methods similar to those reported for purification of antigen-specific antibodies (Hata and Nakayama, 2007; Karlsen et al., 1990) will be employed. Antigen-specific IgA or IgM is subsequently combined with human secretory component.

In a preferred embodiment, the compositions of the invention contain recombinant secretory component, in addition to the IgA and IgM components. Human secretory component can be produced by recombinant techniques (Crottet et al., 1999). The resulting dimeric and polymeric IgA-J chains are purified. The resulting dimeric IgA and the pentameric IgM are further coupled to recombinant secretory component as known to those skilled in the art (Bouvet et al., 1990; Jones et al., 1998; Prinsloo et al., 2006). Pentameric IgM and dimeric IgA containing both J chain and secretory component are again purified by ion-exchange and size exclusion chromatography and/or ultrafiltration as performed by those of skill in the art of protein purification (Corthesy, 1997; Crottet et al., 1999; Lullau et al., 1996). Purified dimeric IgA or pentameric IgM containing secretory component is then enriched in *C. difficile* toxin A and toxin B specific antibodies by affinity purification methods. The purified antigen specific dimeric IgA or pentameric IgM containing secretory component is optionally stabilized for example by the addition of human serum albumin to a final concentration of 5%. The presence of the human J chains and secretory component in the compositions of the invention leads to doses of immunoglobulin A and immunoglobulin M which are more physiologically effective than compositions without such components.

In another embodiment, a pentameric IgM containing component is isolated as a byproduct from hyperimmune pooled human plasma for coupling with secretory component. Hyperimmune pooled human plasma is obtained from donors who have been immunized against a specific disease or are immune to the disease following natural infection.

Pentameric IgM contains 5 IgM monomers per J chain, respectively. Dimeric IgA contains two IgA monomers per J chain.

The antigen specific secretory IgA or IgM antibodies may be administered alone as a liquid or solid, preferably in a solid powder form and preferably in admixture with a carrier to form a pharmaceutical composition such as a tablet, capsule, liquid or suppository.

Since preferred methods of administration are oral and rectal, or enteric installation, and most preferred is oral, with solid oral dosage forms such as tablets and capsules being especially preferred, or enteric installation. These are prepared according to conventional methods known those skilled in the art. The antigen specific secretory IgA or IgM antibodies may also be combined with other pharmaceutically acceptable carriers such as various liquids, proteins or oils which may also provide additional nutritional and/or pharmaceutical benefits. Remington Science and Practice of Pharmacy, $20^{th}$ ed. (2000).

These compositions optionally contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alginates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art; as detailed, for example in U.S. Pat. Nos. 4,017,647; 4,385,078; 4,518, 433; and 4,556,552.

They may contain opacifying agents, and can also be of such composition that they release the active compound or compounds in a certain part of the intestinal tract in a delayed manner. Examples of embedding compositions which can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore melt in the rectum or vaginal cavity and release the active component.

Since the effect of the antigen specific secretory IgA or antigen specific secretory IgM antibody is dependent on its reaching the colon, preferred tablets or capsules are enteric coated. Alternatively, the active antigen specific secretory IgA or antigen specific secretory IgM antibodies can themselves be microencapsulated prior to formulation. Preparation of microcapsules of antigen specific secretory IgA or antigen specific secretory IgM antibody as well as preparation of enteric coated tablets or capsules can be achieved by conventional methods as detailed above.

The antigen specific secretory IgA and antigen specific secretory IgM antibodies mode of action is to bind to and inhibit the *C. difficile* toxins thereby disrupting the virulence pathway of *C. difficile* and removing the toxin from the infected tissue. However for complete elimination of the colonized *C. difficile*, it is also advantageous to administer to patients suffering from *C. difficile* associated diseases a combination of the antigen specific secretory IgA or antigen specific secretory IgM antibodies of the present invention with antibiotics that are known for treating pseudomembranous colitis and/or antibiotic associated diarrhea. Such antibiotics are for example vancomycin, and metronidazole. Because of the prompt elimination of the *C. difficile* toxins, the combination of antigen specific secretory IgA or antigen specific secretory IgM antibody and antibiotic may be synergistic requiring a shorter duration of antibiotic treatment with decreased symptoms, faster symptomatic relief and a lower relapse rate. Recognized doses for administering metronidazole for example is 250 mg four times a day, and oral vancomycin is 125 mg four times a day. Administration of these antibiotics with the antigen specific secretory IgA or antigen specific secretory IgM antibody of the present invention would result in use of substantially reduced dosage of antibiotics.

The administration of such combination antibiotic and antigen specific secretory IgA or antigen specific secretory IgM treatment may be in a single dosage form where both active ingredients are combined and mixed with a pharmaceutically acceptable carrier. Preferred compositions would be those adapted for oral or rectal administration and it would include solid oral dosing forms such as enteric coated tablets or capsules, or suppositories.

The administration of the combination concurrently or following one another in separate dosage forms may still be formulated together in divided tablets or capsules. These are also known to those skilled in the pharmaceutical art.

Treatment of patients suffering from *C. difficile* associated diseases with the combination of two active ingredients can take place not only concurrently in a single or separate dosage form but also following administration of one ingredient with the other. Preferably, administration of the inventive antigen specific secretory IgA or antigen specific secretory IgM is followed by administration of the antibiotic.

The antibody of the present invention is contained in antigen specific secretory IgA or antigen specific secretory IgM provided to a subject suffering *C. difficile* infection or symptoms thereof. In such form, the amount of antigen specific secretory IgA or antigen specific secretory IgM provided to the patient is about 1 gram per day. Typically amounts from about 0.1 to 50 grams per day is used and preferably, 1 to 10 grams per day. For example, about 1 to 2 grams of antigen specific secretory IgA or antigen specific secretory IgM could be given to a subject up to 4 times per day. The doses of the antigen specific secretory IgA or antigen specific secretory IgM antibody formulation to be administered depends upon the subject and the subject's medical history. Dosages of the specific antigen specific secretory IgA or antigen specific secretory IgM for adult humans envisioned by the present invention and considered to be therapeutically effective ranges from between about 0.1 to 500 mg. However, it is to be understood that doses can readily be adjusted to provide appropriate amounts of the antigen specific secretory IgA or antigen specific secretory IgM antibody to any subject, including children.

Diseases and conditions for which administration of the compositions of the invention is to be used therapeutically or prophylatically include, but are not limited to: celiac disease, food allergy and hypersensitivity, common variable immunodeficiency, IgA deficiency, human immunodeficiency virus (HIV) infection, bacterial and viral infections such as lower respiratory tract infection with influenza, lower respiratory tract infection with respiratory syncytial virus, lower respiratory tract infection with rhinovirus, lower respiratory tract infection with adenovirus: protozoan infections such as giadiasis, yeast infections; intestinal infection with *C. difficile*; chronic lymphocytic leukemia; multiple myeloma; macroglobulinemia; chronic bronchitis; bronchiectasis; asthma; immune suppression associated with bone marrow transplantation; immune suppression associated with cyclophosphamide administration; immune suppression associated with azathiaprine administration; immune suppression associated with methotrexate administration; immune suppression associated with chlorambucil administration; immune suppression associated with nitrogen mustard administration; immune suppression associated with 6-mercaptopurine administration; immune suppression associated with thioguanine administration; severe combined immunodeficiency; adenosine deaminase deficiency; major histocompatibility class I (Bare leukocyte syndrome) and class II deficiencies; purine nucleoside phosphorylase deficiency; DiGeorge Syndrome; transient hypogammaglobulinemia of infancy; X-linked agammaglobulinemia; X-linked agammaglobulinemia with growth hormone deficiency; transcobalamin II deficiency; immunodeficiency with thymoma; immunodeficiency with hereditary defective response to Epstein Barr virus; immunoglobulin deficiency with increased IgM; P chain deficiency; ataxia telangiectasia; immunodeficiency with partial albinism; sequelae of selective IgA deficiency such as those due to rheumatoid arthritis; juvenile rheumatoid arthritis; systemic lupus erythematosus; thyroiditis; pernicious anemia; dermatomyositis; Coomb's positive hemolytic anemia; idiopathic Addison's disease; cerebral vasculitis and idiopathic thrombocytopenic purpura.

The invention is further described by reference to the following detailed examples, wherein the methodologies are as described below. These examples are not meant to limit the scope of the invention that has been set forth in the foregoing description. Variations within the concepts of the invention are apparent to those skilled in the art.

EXAMPLE 1

IgA$_1$ Purification

The total IgA$_1$ fraction is purified from the precipitate using the well-established jacalin affinity chromatography method for the separation of IgA$_1$ from IgA$_2$, IgG and IgM from human sera (Haun et al., 1989; Kabir, 1998; Leibl et al., 1996; To et al., 1995). Agarose-bound jacalin with a binding capacity of 1-3 mg IgA/mL gel slurry is obtained commercially (Pierce) and used according to vendor protocol in a gravity-flow column. Briefly, the Cohn Fraction III precipitate is re-suspended in phosphate-buffered saline (PBS) and applied to a bed of jacalin-agarose. The column is washed with PBS until protein in the flow-through portion is no longer detected. The jacalin-bound portion containing the IgA$_1$ is eluted with 0.1 M galactose. Eluate fractions are combined and buffer exchanged (to remove galactose) using either a spin-desalting column (Qiagen) or dialysis. The purity of the IgA$_1$ is assessed by SDS-PAGE and by immunoblot with rabbit anti-human IgA (Pierce). The concentration of IgA$_1$ is determined by an ELISA method using a rabbit anti-human IgA antibody horseradish peroxidase (HP) conjugate (Dako) as described by To et al., 1995).

The isolation of total polyclonal IgM is accomplished by affinity purification of the IgA-depleted Cohn Fraction III material contained in the jacalin column flow-through fractions, using an IgM-specific immobilized mannose binding protein (MBP) gravity-flow column (Pierce) as directed by the manufacturer. Eluate fractions containing die MBP-bound material is combined and buffer exchanged to remove elution components using a spin-desalting column (Qiagen). The purity of the IgM is assessed by SDS-PAGE and by immunoblot with goat anti-IgM antibody alkaline phosphatase conjugate (Pierce).

Polyclonal IgA or IgM is obtained from pooled human plasma following Cohn cold ethanol fractionation to produce fraction III precipitate. IgA or IgM is further purified by adsorption onto an ion exchange medium in neutral or slightly acidic conditions. C. difficile toxins A and B (CalbioChem, Sigma-Aldrich, Promega) are immobilized to an appropriate solid-phase support (Southern Biotechnology, Inc.), with which re-suspended Cohn fraction III precipitate or jacalin-purified IgA solutions are incubated, then washed extensively. Proteins binding only C. difficile toxins A and B are eluted using an appropriate buffer. Methods similar to those reported for purification of antigen-specific antibodies (Hata and Nakamaya, 2007; Karlsen et al., 1990) are used. Antigen specific IGA-J chain dimers and IgM-J chain pentamers are purified. Antigen specific IgA-J chain dimers and IgM-J chain pentamers are then further coupled to recombinant secretory component again by disulfide bonding in mildly oxidizing conditions, preferably at a molar ratio of secretory component to antigen specific IgA-J chain dimers and IgM-J chain pentamers of 1:1. Antigen specific IgA-J chain dimers and IgM containing both J chain and secretory component is again purified. Purified antigen specific IgA-J chain dimers and IgM containing J chain and secretory component is stabilized by the addition of human serum albumin to a final concentration of 5%. The final solution is adjusted to a therapeutic dose of 5 mg IgA or IgM.

An ELISA assay is used to confirm that the IgA and IgM preparations contain specific anti C. dificile IgA or IgM.

EXAMPLE 2

ELISA Methods

An indirect ELISA method to assess the toxin A and B binding capability of IgA and IgM is modeled after published methods (Babcock et al., 2006; Bacon and Fekety, 1994). Human secretory IgA and IgM levels to C. difficile is measured by ELISA using a modification of the methods previously described ((Bacon and Fekety, 1994; Kelly et al., 1992; Leung et al., 1991). Coating antigens used to measure IgA and IgM titers included purified C. difficile toxin A and purified C. difficile toxin.

C. difficile toxins A and B of a toxigenic Clostridium difficile are purified from the broth culture supernatant as previously described (Pothoulakis et al., 1991) or may be obtained commercially (Calbiochem).

The ELISA method is modeled after the method reported by Kelly et al. (Kelly et al., 1992) (paraphrased): Microtiter plates (Immulon II, Dynatech) are coated with C. difficile toxin A or toxin B (each at 10 µg protein per ml in carbonate buffer pH 9.6, 100 µl per well) (Calbiochem) by incubation for 2 hours at 37° C. followed by overnight incubation at 4° C. Plates are washed between each incubation step using phosphate buffered saline with 0.05% Tween 20 (PBS-T). Plates are then blocked with 2% human serum albumin (ICN, 100 µl/well) in PBS and incubated for 1 hour at room temperature.

The Elisa method is modeled after the method reported by Kelly et al. (Kelly et al., 1992) (paraphrased) and is modified herein to include the secondary detection of IgM in brackets [ ]: Horseradish peroxidase-labeled goat anti-human IgA [and IgM] (catalog number STAR98P, AbD Serotec) is used as the secondary antibody (0.2 ug/ml in PBS with 2% human serum albumin) incubated for one hour at 37° C. TMB microwell peroxidase substrate (KPL Laboratories) is used as substrate (100 µl/well) and stopped after 2 to 5 minutes with an equal volume of 1 M phosphoric acid. The optical density is then read at 450 nm with 630 nm as reference using an automated photometer (Dynatech). Controls include substitution of the secondary antibody with peroxidase labeled anti-murine IgA [and IgM] and omission of the peroxidase substrate solution. Results are expressed at the mean optical density of test wells minus mean optical density of background wells (coated with human serum albumin alone).

EXAMPLE 3

Enterotoxicity Method

The following are descriptions of methods to demonstrate that secretory IgA and IgM is capable of inhibiting the enterotoxic effects of C. difficile toxins.

The following method is paraphrased from Pothoulakis (Pothoulakis et al., 1991) and Bostwick and Hoerr (U.S. Pat. No. 5,773,000) and is modified to include the agents of relevance in this application, IgA, and IgM, in brackets [ ]: Fasting male Wistar rats are anesthetized by intraperitoneal injection of sodium pentobarbital. Laparotomy is performed, the renal pedicles tied and 3H-mannitol (10 µCi, PerkinElmer Life Sciences, Boston, Mass.) administered intravenously. Closed ileal loops (5 cm) are then formed and injected with 400 µl of 50 mM Tris buffer (pH 7.4) or with Tris buffer containing *C. difficile* culture filtrate (20 ug of protein). The inhibitory effect of secretory IgA [and IgM] is assessed by the addition of secretory IgA [and IgM] (200 ug) to the toxins prior to injection into the ileal lumen.

The following method is paraphrased from Pothoulakis (Pothoulakis et al., 1991) and Bostwick and Hoerr (U.S. Pat. No. 5,773,000) and is modified to include the agents of relevance in this application: The abdominal incision is closed and anesthesia maintained with sodium pentobarbital. The animals are sacrificed after 4 hours and the ileal loops immediately harvested. Loop weight to length ratio is determined as a measure of enterotoxin effect. Mannitol excretion, indicating intestinal permeability, is measured by counting radioactivity in the luminal fluid. Ileal tissue samples are also fixed in formalin, paraffin-embedded and sections stained with hematoxylin and eosin. The histologic severity of enteritis is graded taking into account the following features: i) neutrophil margination and tissue infiltration, ii) hemorrhagic congestion and edema of the mucosa, iii) epithelial cell damage. A score of 0 to 3 denotes increasingly severe pathological changes.

EXAMPLE 4

In Vitro Cellular Cytotoxicity Method

For development of the cell-based assay, the human colon carcinoma T84 cell line (ATCC), which has been used previously to investigate the mechanisms of toxins A and B toxicity (Chaves-Olarte et al., 1997; Stubbe et al., 2000), is used. Following the method of Chaves-Olarte et al., a cytotoxic titer of toxins A and B (Calbiochem) is performed. Based on these cytotoxicity studies, the optimal concentrations of toxins A and B for use in our IgA/IgM neutralization assay is determined. The toxin neutralization assay follows essentially the method described by Babcock with some modification (Babcock et al., 2006). Here, T84 cells are grown to sub-confluence in a 48-well cell culture plate at 37° C. in a humidified 5% $CO_2$ atmosphere. Toxins A or B (at optimal concentrations determined above) are pre-incubated with variable concentrations of IgA or IgM antibody for 1 h, after which the mixture is incubated with the cell cultures for the growth period leading to confluence. Post-confluence, the cultures are examined for cytotoxic morphology changes (cell rounding, determined microscopically) and cell viability (determined by the exclusion of trypan blue) and compared to appropriate control experiments (toxin or antibody alone). Once optimal toxin and antibody concentrations are determined using the above assays, antibody protection of cell viability is confirmed using a lactate dehydrogenase activity cell cytotoxicity assay (LDH Cell Cytotoxicity Assay Service, Catalog #10011919, Cayman Chemical Company, Ann Arbor, Mich.).

EXAMPLE 5

Human Treatment—Treatment of a Person Ill with *C. difficile* Associated Disease with Secretory IgM An adult individual ill with *C. difficile* associated disease is treated with secretory pentameric IgM containing antibody activity against *C. difficile* toxin. Treatment is with 1 gram orally three times daily together with vancomycin in appropriate dosage. Treatment is continued until symptoms resolve and the stool becomes negative for *C. difficile* toxin.

REFERENCES

Babcock, G. J., Broering, T. J., Hernandez, H. J., Mandell, R. B., Donahue, K., Boatright, N., Stack, A. M., Lowy, I., Graziano, R., Molrine, D., Ambrosino, D. M., and William D. Thomas, W. D. (2006). Human Monoclonal Antibodies Directed against Toxins A and B Prevent *Clostridium difficile*-Induced Mortality in Hamsters. *Infect Immun.* 74, 6339-6347.

Bacon, A. E., and Fekety, R. (1994). Immunoglobulin G Directed Against Toxins A and B of *Clostridium difficile* in the General Population and Patients with Antibiotic-Associated Diarrhea. *Diagn Microbiol Infect Dis* 18, 205-209.

Barroso, L. A., Wang, S. Z., Phelps, C. J., Johnson, J. L., and Wilkins, T. D. (1990). Nucleotide sequence of *Clostridium difficile* toxin B gene. *Nucleic Acids Research* 18, 4004.

Bartlett, J. G. (2006). Treatment of *Clostridium difficile*-associated disease (CDAD). *Med. Lett. Drugs Ther.* 48, 89-90, 92.

Boesman-Finkelstein, M., Walton, N. E., and Finkelstein, R. A. (1989). Bovine lactogenic immunity against cholera toxin-related enterotoxins and *Vibrio cholerae* outer membranes. *Infect. Immun.* 57, 1227-1234.

Borriello, S. P. (1998). Pathogenesis of *Clostridium difficile* infection. *J Antimicrob. Chemother.* 41, 13-19.

Bostwick E. F. and Hoerr R. A. (U.S. Pat. No. 5,773,000)

Bouvet, J. P., Pillot, J., and Iscaki, S. (1990). Secretory component-binding properties of normal serum IgM. *Scand. J. Immunol.* 31, 437-441.

Brussow, H., Hilpert, H., Walther, I., Sidoti, J., Mietens, C., and Bachmann, P. (1987). Bovine milk immunoglobulins for passive immunity to infantile rotavirus gastroenteritis. *J. Clin. Microbiol.* 25, 982-986.

Carayannopoulos, L., and Capra, J. D. (1993). "Immunoglobulins: structure and function. In Fundamental Immunology" Lippincott Williams & Wilkins, New York.

Chaves-Olarte, E., Weidmann, M., Eichel-Streiber, C. v., and Thelestam, M. (1997). Toxins A and B from *Clostridium difficile* Differ with Respect to Enzymatic Potencies, Cellular Substrate Specificities, and Surface Binding to Cultured Cells. *J. Clin. Invest.* 100, 1734-1741.

Cohn, E. J., Strong, L. E., Hughes Jr., W. L., Mulford, D. J., Ashworth, J. N., Melin, M., and Taylor, H. L. (1946). A System for the Separation into Fractions of the Protein and Lipoprotein Components of Biological Tissues and Fluids. *J. Am. Chem. Soc.* 68, 459-475.

Cone, L. A., Lopez, C., Tarleton, H. L., Jodoin, D., Taylor, M., Gade-Andavolu, R., and Dreisbach, L. P. (2006). A durable response to relapsing *Clostridium difficile* colitis may require combined therapy with high-dose oral vancomycin and intravenous immune globulin. *Infect Dis Clin Pract* 14, 217-220.

Corthesy, B. (1997). Recombinant secretory IgA for immune intervention against mucosal pathogens. *Biochem. Soc. Trans.* 25, 471-475.

Crottet, P., Cottet, S., and Corthesy, B. (1999). Expression, purification and biochemical characterization of recombinant murine secretory component, a novel tool in mucosal immunology. *Biochem. J.* 341, 299-306.

Delacroix D. L., Hodgson H. J., McPherson A., Dive C., Vaerman J. P. Selective transport of polymeric immunoglobulin A in bile. Quantitative relationships of monomeric and polymeric immunoglobulin A, immunoglobulin M, and other proteins in serum, bile, and saliva. J. Clin. Invest. 1982 August; 70(2):230-41

Delacroix D. L., Elkom K. B., Geubel A. P., Hodgson H. F., Dive C., Vaerman J. P. Changes in size, subclass, and metabolic properties of serum immunoglobulin A in liver diseases and in other diseases with high serum immunoglobulin A. J. Clin. Invest. 1983 February; 71(2):358-67.

Dove, C. H., S. Z., W., Price, S. B., Phelps, C. J., Lyerly, D. M., Wilkins, T. D., and Johnson, J. L. (1990). Molecular characterization of the *Clostridium difficile* toxin A gene. OInfect. Immun. 58, 480-488.

Fayer, R., Guidry, A., and Blagburn, B. L. (1990). Immunotherapeutic efficacy of bovine colostral immunoglobulins from a hyperimmunized cow against cryptosporidiosis in neonatal mice. Infect. Immun. 58, 2962-2965.

Hata, T., and Nakayama, M. (2007). Rapid single-tube method for small-scale affinity purification of polyclonal antibodies using HaloTag technology. J. Biochem. Biophys. Methyl. 70, 679-682.

Haun, M., Incledon, B., Alles, P., and Wasi, S. (1989). A rapid procedure for the purification of IgA1 and IgA2 subclasses from normal human serum using protein G and jackfruit lectin (jacalin) affinity chromatography. Immunol Lett. 22, 273-279.

Hilpert, H., Brussow, H., Mietens, C., Sidoti, J., Lerner, L., and Werchau, H. (1987). Use of bovine milk concentrate containing antibody to rotavirus to treat rotavirus gastroenteritis in infants. J. Infect. Dis. 156, 158-166.

Johnson, S., Sypura, W. D., Gerding, D. N., Ewing, S. L., and Janoff, E. N. (1995). Selective neutralization of a bacterial enterotoxin by serum immunoglobulin A in response to mucosal disease, Infect, Immun. 63, 3166-3173.

Jones, R. M. L., Schweikart, F., Frutiger, S., Jaton, J.-C., and Hughes, G. J. (1998). Thiol-disulfide redox buffers maintain a structure of immunoglobulin A that is essential for optimal in vitro binding to secretory component. Biochem Biophys Acta. 1429, 265-274.

Kabir, S. (1998). Jacalin: a jackfruit (Artocarpus heterophyllus) seed-derived lectin of versatile applications in immunobiological research. J Immunol Methods 212, 193-211.

Karlsen, A., Lernmark, A., Kofod, H., and Dyrberg, Y. (1990). A novel affinity purification method to isolate peptide specific antibodies. J. Immunol. Methods J. Immunol. Methods 128, 151-157.

Kelly, C. P., Pothoulakis, C., Orellana, J., and LaMont, J. T. (1992). Human colonic aspirates containing immunoglobulin A antibody to *Clostridium difficile* toxin A inhibit toxin A-receptor binding. Gastroenterology 102, 35-40.

Leibl, H., Tomasits, R., Wolf, H. M., Eibl, M. M., and Mannhalter, J. W. (1996). Method for the isolation of biologically active monomeric immunoglobulin A from a plasma fraction, J Chromatogr B Biomed Appl. 678, 173-180.

Leung, D. Y., Kelly, C. P., Boguniewicz, M., Pothoulakis, C., LaMont, J, T., and Flores, A. (1991). Treatment with intravenously administered gamma globulin of chronic relapsing colitis induced by *Clostridium difficile* toxin. J Pediatr. 118, 633-637.

Libby, J. M., Jortner, B. S., and Wilkins, T. D. (1982). Effects of the two toxins of *Clostridium difficile* in antibiotic-associated cecitis in hamsters. Infect. Immun. 36, 822-829.

Louie, T. J., Peppe, J., Watt, C. K., Johnson, D., Mohammed, R., Dow, G., Weiss, K., Simon, S., John, J, F. J., Garber, G., Chasan-Taber, S., and Davidson, D. M. (2006). Tolevamer Study Investigator Group. Tolevamer, a novel nonantibiotic polymer, compared with vancomycin in the treatment of mild to moderately severe *Clostridium difficile*-associated diarrhea. Clin. Infect Dis. 43, 411-420.

Lullau, E, Heyse, S., Vogel, H., Marison, I., von Stockar, U., Kraehanbuhl, J.-P., and Corthesy, B. (1996). Antigen binding properties of purified immunogloulin A antibodies. J. Biol. Chem., 16300-16309.

Lyerly, D. M., Bostwick, E. F., Binion, S. B., and Wilkins, T. D. (1991). Passive immunization of hamsters against disease caused by *Clostridium difficile* by use of bovine immunoglobulin G concentrate. Infect. Immun. 59, 2215-2218.

Lyerly, D. M., Krivan, H. C., and Wilkins, T. D. (1988). *Clostridium difficile*: its disease and toxins. Clin. Microbiol. Rev. 1, 1-18.

McPherson, S., Rees, C. J., Ellis, R., Soo, S., and Panter, S. J. (2006). Intravenous immunoglobulin for the treatment of severe, refractory, and recurrent *Clostridium difficile* diarrhea. Dis Colon Rectum. 49, 640-645.

Mietens, C., Keinhorst, H., Hilpert, H., Gerber, H., Amster, H., and Pahud, J. J. (1979). Treatment of infantile *E. coli* gastroenteritis with specific bovine anti-*E. coli* milk immunoglobulins. Eur. J Pediatr. 132, 239-252.

Oncley, J. L., Melin, M., Richert, D. A., Cameron, J. W., and Gross, P. M. J. (1949). The separation of the antibodies, isoagglutinins, prothrombin, plasminogen and $\beta$1-lipoprotein into subfractions of human plasma. J Am. Chem. Soc. 71.

Pothoulakis, C., LaMont, J. T., Eglow, R., Gao, N., Rubins, J. B., Theoharides, T. C., and Dickey, B. F. (1991). Characterization of rabbit ileal receptors for *Clostridium difficile* toxin A. Evidence for a receptor-coupled G protein. J. Clin. Invest. 88, 119-125.

Prinsloo, E., Oosthuizen, V., Muramoto, K., and Naude, R. J. (2006). In vitro refolding of recombinant human free secretory component using equilibrium gradient dialysis. Protein Expr. Purif. 47, 179-185.

Salcedo, J., Keates, S., Pothoulakis, C., Warny, M., Castagliuolo, I., LaMont, J. T., and Kelly, C. P. (1997). Intravenous immunoglobulin therapy for severe *Clostridium difficile* colitis. Gut 41, 366-370.

Saturno E. J., Costa H., Sorensen R. Oral Immunoglobulin Therapy in a Child with Severe *Clostridium Difficile* Diarrhea. J Allergy Clin Immunol 2006; 117:S284.

Strong, L. E. (1963). "Blood Fractionation." Interscience Publishers, New York.

Stubbe, H., Berdoz, J., Kraehenbuhl, J.-P., and Corthesy, B. (2000). Polymeric IgA Is Superior to Monomeric IgA and IgG Carrying the Same Variable Domain in Preventing *Clostridium difficile* Toxin A Damaging of T84 Monolayers. J Immunol 164, 1952-1960.

Tacket, C. O., Losonsky, G., Link, H., Hoang, Y., Guesry, P., Hilpert, H., and Levine, M. M. (1988). Protection by milk immunoglobulin concentrate against oral challenge with enterotoxigenic *Escherichia coli*. N. Eng. J. Med. 318, 1240-1243.

Tjellström, B., Stenhammar, L., Eriksson, S., and Magnusson, K. E. (1993). Oral immunoglobulin A supplement in treatment of *Clostridium difficile* enteritis. Lancet 341, 701-702.

To, W. Y., Leung, J. C., and Lai, K. N. (1995). Identification and characterization of human serum alpha2-HS glycoprotein as a jacalin-bound protein. Biochim Biophys Acta. 1249, 58-64.

Wilcox, M. H. (2004). Descriptive study of intravenous immunoglobulin for the treatment of recurrent *Clostridium difficile* diarrhea. J Antimicrob Chemoth. 53, 882-884.

Yoshiyama, Y., and Brown, W. R. (1987). Specific antibodies to cholera toxin in rabbit milk are protective against *Vibrio cholerae*-induced intestinal secretion. Immunology. *Immunology* 61, 543-547.

Patent applications and publications mentioned in the specification are indicative of the levels of those skilled in the art to which the invention pertains. These applications and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A composition comprising antigen specific polyclonal IgM-J chain pentamers;
    the antigen specific polyclonal IgM-J chain pentamers, combined with a recombinant secretory component in a molar ratio of the antigen specific IgM-J chain pentamers to the secretory component of 1:1 forming an antigen specific secretory pentameric IgM.

2. The composition of claim 1 wherein the antigen specific IgM-J chain pentamers are combined with said recombinant secretory component by a disulfide linkage.

3. The composition of claim 1 further comprising excipients to form a tablet, a capsule, a liquid oral dosing form, a suppository.

4. The composition of claim 1, further comprising a microencapsulant encompassing said antigen specific secretory pentameric IgM.

5. The composition of claim 3 further comprising an antibiotic.

6. The composition of claim 5 wherein said antibiotic is at least one of vancomycin or metronidazole.

7. A process for treating *C. difficile* associated disease in a human comprising:
    administering to said human an amount of a composition consisting of antigen specific polyclonal IgM-J chain pentamers;
    the antigen specific polyclonal IgM-J chain pentamers, combined with a recombinant secretory component in a molar ratio of the antigen specific IgM-J chain pentamers to the secretory component of 1:1 forming an antigen specific secretory pentameric IgM wherein said composition binds to a toxin produced by *C. difficile*.

8. The process of claim 7 further comprising administering an antibiotic in concert with the antigen specific secretory pentameric IgM.

9. The process of claim 8 wherein the antibiotic is administered and discontinued prior to the administration of the composition.

10. A composition comprising:
    antigen specific polyclonal IgA-J chain dimers;
    the antigen specific polyclonal IgA-J chain dimers combined with a recombinant secretory component in a molar ratio of the antigen specific IgA-J chain dimers to the secretory component of 1:1 forming an antigen specific secretory dimeric IgA.

11. The composition of claim 10 wherein the antigen specific IgA-J chain dimers are combined with said recombinant secretory component by a disulfide linkage.

12. The composition of claim 10 further comprising excipients to form a tablet, a capsule, a liquid form oral dose, or a suppository.

13. The composition of claim 10, further comprising a microencapsulant encompassing said secretory antigen specific dimeric IgA.

14. The composition of claim 12 further comprising an antibiotic present in said tablet or capsule.

15. A process for treating *C. difficile* associated disease in a human comprising:
    administering to said human suffering therefrom a therapeutically effective amount of a composition consisting of antigen specific polyclonal IgA-J chain dimers;
    the antigen specific polyclonal IgA-J chain dimers combined with a recombinant secretory component in a molar ratio of the antigen specific IgA-J chain dimers to the secretory component of 1:1 forming an antigen specific secretory dimeric IgA wherein said composition binds to a toxin produced by *C. difficile*.

16. The process of claim 15 further comprising administering an antibiotic.

17. The process of claim 15, further comprising administering an antibiotic, wherein the antibiotic is administered and discontinued prior to the administration of the composition of claim 15.

* * * * *